(12) United States Patent
Yamauchi et al.

(10) Patent No.: US 11,630,059 B2
(45) Date of Patent: Apr. 18, 2023

(54) INTERFERENCE IMAGE ACQUIRING DEVICE AND METHOD FOR ACQUIRING INTERFERENCE IMAGE

(71) Applicants: HAMAMATSU PHOTONICS K.K., Hamamatsu (JP); NATIONAL UNIVERSITY CORPORATION HAMAMATSU UNIVERSITY SCHOOL OF MEDICINE, Hamamatsu (JP)

(72) Inventors: Toyohiko Yamauchi, Hamamatsu (JP); Kentaro Goto, Hamamatsu (JP); Hisayuki Matsui, Hamamatsu (JP); Satoshi Hirakawa, Hamamatsu (JP); Hidenao Yamada, Hamamatsu (JP)

(73) Assignees: HAMAMATSU PHOTONICS K.K., Hamamatsu (JP); NATIONAL UNIVERSITY CORPORATION HAMAMATSU UNIVERSITY SCHOOL OF MEDICINE, Hamamatsu (JP)

( * ) Notice: Subject to any disclaimer, the term of this patent is extended or adjusted under 35 U.S.C. 154(b) by 449 days.

(21) Appl. No.: 16/962,024

(22) PCT Filed: Nov. 22, 2018

(86) PCT No.: PCT/JP2018/043207
§ 371 (c)(1),
(2) Date: Jul. 14, 2020

(87) PCT Pub. No.: WO2019/142492
PCT Pub. Date: Jul. 25, 2019

(65) Prior Publication Data
US 2020/0400562 A1 Dec. 24, 2020

(30) Foreign Application Priority Data
Jan. 16, 2018 (JP) .............................. JP2018-004681

(51) Int. Cl.
*G01B 9/02* (2022.01)
*G01N 21/45* (2006.01)
(Continued)

(52) U.S. Cl.
CPC ............. *G01N 21/45* (2013.01); *C12M 41/46* (2013.01); *C12N 5/0062* (2013.01); *G01B 9/02041* (2013.01); *H04N 5/369* (2013.01)

(58) Field of Classification Search
CPC ...... G01N 21/45; G01B 9/02041; G01B 9/02; G02B 21/0056; G02B 21/0088
See application file for complete search history.

(56) References Cited

U.S. PATENT DOCUMENTS 5,357,341 A * 10/1994 Kuchel ............. G01B 9/02087
356/520
2013/0010283 A1 1/2013 Villiger et al.
(Continued)

FOREIGN PATENT DOCUMENTS

| CN | 1798996 A | 7/2006 |
|---|---|---|
| CN | 201732057 U | 2/2011 |

(Continued)

OTHER PUBLICATIONS

Kim, Taewoo, et al., "White-light diffraction tomography of unlabelled live cells," Nature Photonics, 8, 2014, p. 256-p. 263.
(Continued)

*Primary Examiner* — Jonathan M Hansen
(74) *Attorney, Agent, or Firm* — Faegre Drinker Biddle & Reath LLP

(57) ABSTRACT

An interference image acquisition apparatus includes a light source, a beam splitter, a second reflection mirror, an imager, and a first reflection mirror. A cell is placed on one side of a transparent material, and the first reflection mirror is placed on the other side of the transparent material. In a
(Continued)

two-beam interferometer, an optical path difference between an optical path length of a first light beam reflected by the first reflection mirror and an optical path length of a second light beam reflected by the second reflection mirror is set to a coherence length of light output from the light source or less. The imager acquires an interference image in a state in which the cell is placed at a position conjugate to an imaging plane in a first optical system between the imaging plane and the first reflection mirror.

22 Claims, 14 Drawing Sheets

(51) Int. Cl.
  *C12M 1/34* (2006.01)
  *C12N 5/00* (2006.01)
  *H04N 5/369* (2011.01)

(56) References Cited

U.S. PATENT DOCUMENTS

| | | | | |
|---|---|---|---|---|
| 2013/0093871 A1* | 4/2013 | Nowatzyk | | G02B 21/26 348/79 |
| 2016/0048010 A1* | 2/2016 | Nowatzyk | | G02B 5/32 359/224.1 |
| 2016/0123719 A1* | 5/2016 | Novak | | G01B 9/02067 356/125 |
| 2020/0400504 A1* | 12/2020 | Maruno | | G01J 3/4535 |
| 2021/0364432 A1* | 11/2021 | Pruneri | | G01N 21/553 |

FOREIGN PATENT DOCUMENTS

| | | |
|---|---|---|
| CN | 103415755 A | 11/2013 |
| CN | 103842769 A | 6/2014 |
| CN | 204388780 U | 6/2015 |
| CN | 107121092 A | 9/2017 |
| CN | 107209000 A | 9/2017 |
| CN | 107209001 A | 9/2017 |
| JP | S57-173704 A | 10/1982 |
| JP | 2016-519940 A | 7/2016 |
| WO | WO-2014/190303 A1 | 11/2014 |
| WO | WO-2016/121250 A1 | 8/2016 |

OTHER PUBLICATIONS

International Preliminary Report on Patentability dated Jul. 30, 2020 for PCT/JP2018/043207.

* cited by examiner

INTERFERENCE IMAGE ACQUIRING DEVICE AND METHOD FOR ACQUIRING INTERFERENCE IMAGE

TECHNICAL FIELD

The present disclosure relates to an apparatus and a method for acquiring an interference image of an object.

BACKGROUND ART

Patent Document 1 discloses an invention of an apparatus and a method that can acquire an interference image of an object. The interference image acquisition apparatus described in this document includes a light source, a two-beam interferometer that splits light output from the light source into two light beams, then combines the two light beams, and outputs interference light, and an imager that receives the interference light output from the two-beam interferometer. Further, the interference image acquisition apparatus can also acquire a phase image or the like of the object using a phase shift method. That is, the interference image acquisition apparatus achieves a state in which an optical path difference between the two light beams in the two-beam interferometer is stabilized by each of a plurality of set values different from each other, an interference image of the object is acquired by the imager in each of the states, and determines a phase image or the like based on the plurality of acquired interference images.

CITATION LIST

Patent Literature

Patent Document 1: International Publication No. 2016-121250

Non Patent Literature

Non Patent Document 1: Taewoo Kim et al., "White-light diffraction tomography of unlabelled live cells", Nature Photonics 8, 2014, pp. 256-263

SUMMARY OF INVENTION

Technical Problem

Conventionally, a reflection enhancing coating is provided on an inner side of a bottom portion of a container in which an object is contained, and the object is placed on the reflection enhancing coating. Then, a first light beam that is one of the two light beams in the two-beam interferometer is transmitted through the object, reflected by the reflection enhancing coating, again transmitted through the object, and then combined with a second light beam that is another. However, for example, in a case where the object is a cell, cells are cultured on the reflection enhancing coating provided on the inner side of the bottom portion of the container, and the culture environment in this case is sometimes unfavorable for the cells.

In a case where cells are cultured in an environment suited to the culture of cells and then the interference image of the cells is acquired or the phase image or the like is acquired, it is necessary to place a reflection mirror that reflects the first light beam apart from the cells. In the conventional techniques, in a case where the reflection mirror and the object are apart from each other as described above, it is difficult to acquire a clear interference image or the like.

An object of an embodiment is to provide an apparatus and a method that can acquire a clear interference image in a case where a reflection mirror and an object are apart from each other.

Solution to Problem

An embodiment is an interference image acquisition apparatus. The interference image acquisition apparatus includes (1) a light source for outputting incoherent light, (2) a two-beam interferometer for splitting the light output from the light source into a first light beam and a second light beam, combining the first light beam transmitted through an object placed on an optical path of the first light beam and reflected by a first reflection mirror and the second light beam reflected by a second reflection mirror, and outputting interference light, and (3) an imager having an imaging plane for receiving the interference light output from the two-beam interferometer, the imager for acquiring an interference image of the object, and (4) in the two-beam interferometer, the first reflection mirror is placed apart from the object, and an optical path difference between an optical path length of the first light beam reflected by the first reflection mirror and an optical path length of the second light beam reflected by the second reflection mirror is set to a coherence length of the light output from the light source or less, and the imager acquires the interference image in a state in which the object is placed at a position conjugate to the imaging plane in a first optical system between the imaging plane and the first reflection mirror.

An embodiment is an interference image acquisition method. The interference image acquisition method includes (1) an interference step of, in a two-beam interferometer, splitting incoherent light output from a light source into a first light beam and a second light beam, combining the first light beam transmitted through an object placed on an optical path of the first light beam and reflected by a first reflection mirror and the second light beam reflected by a second reflection mirror, and outputting interference light, and (2) an imaging step of acquiring an interference image of the object by an imager having an imaging plane for receiving the interference light output from the two-beam interferometer, and (3) in the interference step, in the two-beam interferometer, the first reflection mirror is placed apart from the object, and an optical path difference between an optical path length of the first light beam reflected by the first reflection mirror and an optical path length of the second light beam reflected by the second reflection mirror is set to a coherence length of the light output from the light source or less, and in the imaging step, the interference image is acquired by the imager in a state in which the object is placed at a position conjugate to the imaging plane in a first optical system between the imaging plane and the first reflection mirror.

Advantageous Effects of Invention

According to the embodiment, a clear interference image can be acquired in a case where a reflection mirror and an object are apart from each other.

DESCRIPTION OF EMBODIMENTS

Hereinafter, embodiments of an interference image acquisition apparatus and an interference image acquisition method will be described in detail with reference to the accompanying drawings. In the description of the drawings, the same elements will be denoted by the same reference signs, without redundant description. The present invention is not limited to these examples.

Figure 1:
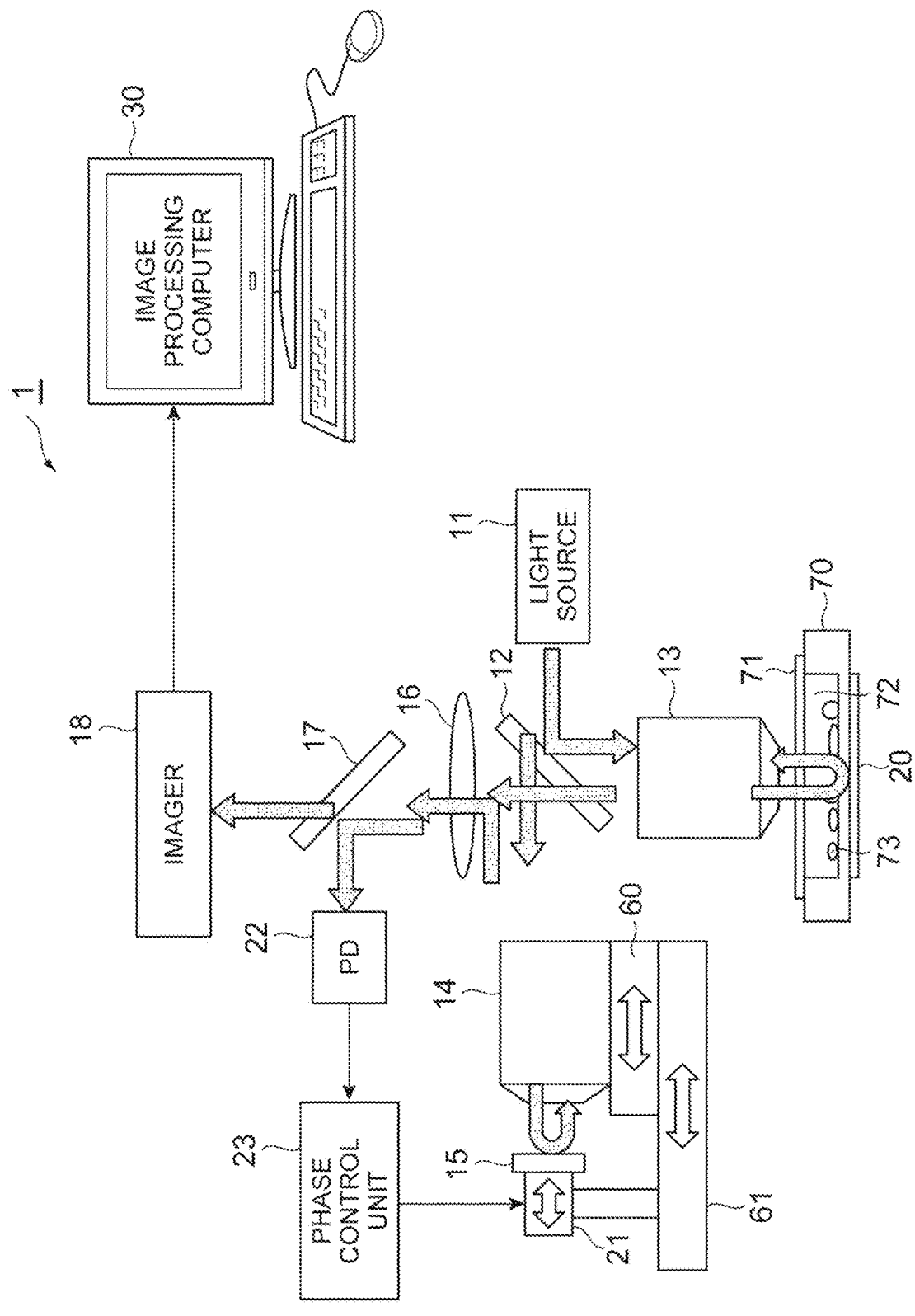
FIG. 1 is a diagram illustrating a configuration of an interference image acquisition apparatus 1.

FIG. 1 is a diagram illustrating a configuration of an interference image acquisition apparatus 1. The interference image acquisition apparatus 1 includes a light source 11, a beam splitter 12, an objective lens 13, an objective lens 14, a second reflection mirror 15, a tube lens 16, a beam splitter 17, an imager 18, a first reflection mirror 20, a piezoelectric element 21, a photodetector 22, a phase control unit 23, an operation unit 30, a focus adjustment mechanism 60, and an optical path difference adjustment mechanism 61. The interference image acquisition apparatus 1 has a Michelson interferometer that is a two-beam interferometer, and acquires an interference image of an object.

The object is not limited to a specific cell or a biological sample. Examples of the object include a cultured cell, an immortalized cell, a primary cultured cell, a cancer cell, a fat cell, a liver cell, a cardiac muscle cell, a nerve cell, a glia cell, a somatic stem cell, an embryonic stem cell, a pluripotential stem cell, an iPS cell, and a cell aggregation (a colony or spheroid) generated based on the cells. Further, the object is not limited to a biological object, and includes an industrial sample, for example, an inside of glass, an inside of a semiconductor element, an inside of a resin material, a liquid crystal, and a high molecular compound.

In the following description of the present embodiment, as a configuration example of the sample illustrated in FIG. 2, assuming that the object is a cell 73 in a culture solution 72 contained in a container 70. The inside of the container 70 is sealed with a cover 71. On the outer side of the bottom portion (transparent material) of the container 70, the first reflection mirror 20 is placed.

The light source 11 outputs incoherent light. Examples of the light source 11 include a lamp light source such as a halogen lamp, a light emitting diode (LED) light source, a super luminescent diode (SLD) light source, and an amplified spontaneous emission (ASE) light source.

The beam splitter 12 is optically coupled to the light source 11, and constitutes a Michelson interferometer that is a two-beam interferometer. The beam splitter 12 may be a half mirror, for example, in which the ratio of the transmittance and the reflectance is 1:1. The beam splitter 12 splits the light output from the light source 11 into two light beams to form a first light beam and a second light beam. The beam splitter 12 outputs the first light beam to the objective lens 13, and outputs the second light beam to the objective lens 14.

Further, the beam splitter 12 receives the first light beam reflected by the first reflection mirror 20 and passed through the objective lens 13, and receives the second light beam reflected by the second reflection mirror 15 and passed through the objective lens 14. Then, the beam splitter 12 combines the incident first light beam and the second light beam, and outputs interference light to the tube lens 16.

The objective lens 13 is optically coupled to the beam splitter 12, and focuses the first light beam output from the beam splitter 12 to the cell 73 in the container 70. Further, the objective lens 13 receives the first light beam reflected by the first reflection mirror 20, and outputs the first light beam to the beam splitter 12.

The objective lens 14 is optically coupled to the beam splitter 12, and outputs the second light beam output from the beam splitter 12 to the second reflection mirror 15. Further, the objective lens 14 receives the second light beam reflected by the reflection surface of the second reflection mirror 15, and outputs the second light beam to the beam splitter 12. The focus adjustment mechanism 60 moves the objective lens 14 relatively to the second reflection mirror 15 along the optical axis direction, and thus can adjust the distance between the objective lens 14 and the second reflection mirror 15. The optical path difference adjustment mechanism 61 moves the objective lens 14, the second reflection mirror 15, and the focus adjustment mechanism 60 along the optical axis direction, and thus can adjust the optical path difference between the first light beam and the second light beam.

The tube lens 16 is optically coupled to the beam splitter 12 that constitutes the two-beam interferometer, and forms an image of the interference light output from the beam splitter 12 on the imaging plane of the imager 18 through the beam splitter 17. The beam splitter 17 splits the light reached from the tube lens 16 into two beams, outputs one light beam to the imager 18, and outputs the other light beam to the photodetector 22. The beam splitter 17 may be a half mirror, for example.

The imager 18 is optically coupled to the beam splitter 17, receives the interference light reached from the beam splitter 17, and acquires an interference image. For example, the imager 18 is an image sensor, such as a CCD area image sensor and a CMOS area image sensor.

The piezoelectric element 21 moves the reflection surface of the second reflection mirror 15 in the direction perpendicular to the reflection surface. The piezoelectric element 21 can adjust the optical path difference (that is, the phase difference) between the two light beams in the two-beam interferometer by moving the reflection surface. The piezoelectric element 21 can determine the position of the reflection surface of the second reflection mirror 15 with the resolution less than the wavelength. In the two-beam interferometer, the optical path difference between two light beams is variable.

In addition, assuming that the optical distance from the beam splitter 12 to the first reflection mirror 20 is L1, and the optical distance from the beam splitter 12 to the reflection surface of the second reflection mirror 15 is L2, the optical path difference between the two light beams in the two-beam interferometer is 2(L1−L2). When the optical path difference is the coherence length of the output light of the light source 11 or less, the imager 18 can acquire a clear interference image. In adjusting the optical path difference, in a case where the necessary adjustment width of the optical path difference is larger than the movable distance of the piezoelectric element 21, the optical path difference adjustment mechanism 61 may be used.

The coherence length of the output light of the light source 11 is inversely proportional to the wavelength bandwidth of the light source 11. For example, when the light source 11 is a halogen lamp, the coherence length is approximately 1 μm, when the light source 11 is an LED light source, the coherence length is approximately 3 μm, and when the light source 11 is an SLD light source or an ASE light source, the coherence length is approximately 10 to 50 μm. When the center wavelength of the output light of the light source 11 is λ0, a phase difference Δϕ between the two light beams in the two-beam interferometer is expressed by the following Formula.

[Formula 1]

$$\Delta\phi = 2\pi \times 2 \times (L1-L2)/\lambda 0 \quad (1)$$

The photodetector 22 is optically coupled to the beam splitter 17, receives the interference light reached from the beam splitter 17, and outputs a detection signal. Examples of the photodetector 22 include a photodiode, avalanche photodiode, and photomultiplier tube, and further, may include a line sensor (linear sensor), CCD area image sensor, CMOS area image sensor, and any other sensor.

The phase control unit 23 is electrically coupled to the photodetector 22, and receives the detection signal output from the photodetector 22. Further, the phase control unit 23 is electrically coupled to the piezoelectric element 21, and controls the adjustment operation of the optical path difference by the piezoelectric element 21. The phase control unit 23 detects the optical path difference between the two light beams in the two-beam interferometer based on the received detection signal. Then, the phase control unit 23 controls the adjustment operation of the optical path difference by the piezoelectric element 21 by feedback control based on the detection result. Thus, a state (a locked state) can be achieved in which the optical path difference between the two light beams in the two-beam interferometer is stabilized at the set value.

The imager 18 can acquire the interference image of the object (cell 73) by imaging in the locked state. The operation unit 30 can determine the complex amplitude image, the phase image, and the intensity image of the object based on the interference image acquired by the imager 18. The operation unit 30 may be a computer, such as a personal computer and a tablet terminal, including a processor (for example, a CPU) and a storage unit (for example, a RAM or a storage). Further, the operation unit 30 may be a microcomputer or an FPGA. Further, the operation unit 30 may include an input unit (a keyboard, a mouse, and a tablet terminal, for example) that accepts inputs from an operator, and a display unit (a display, and a tablet terminal, for example) that displays the interference image and the phase image, and the like. Further, the operation unit 30 preferably has functions that displays images on a screen and accepts the instruction of a region on the screen by the operator.

Figure 2:
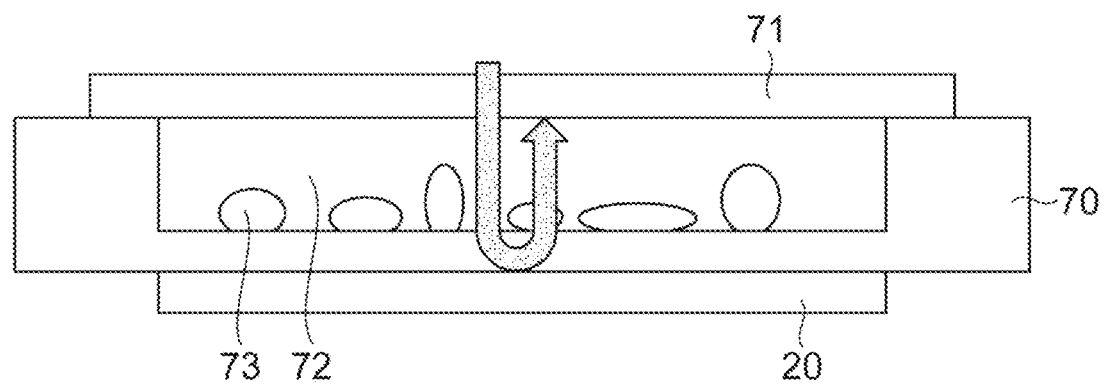
FIG. 2 is a diagram illustrating a configuration of a sample.

In the present embodiment, as illustrated in FIG. 2, the cells 73 are placed on one side of the transparent material (bottom portion of the container 70), and the first reflection mirror 20 is placed on the other side of the transparent material. That is, the first reflection mirror 20 is placed apart from the cell 73 that is the object. Further, in the two-beam interferometer, the optical path difference between the optical path length of the first light beam reflected by the first reflection mirror 20 and the optical path length of the second light beam reflected by the second reflection mirror 15 is set to the coherence length of the light output from the light source 11 or less (interference step). In adjusting the optical path difference, the extension or contraction of the piezoelectric element 21 may be used, or the optical path difference adjustment mechanism 61 may be used.

Further, the imager 18 acquires the interference image in a state in which the cell 73 is placed at a position conjugate to the imaging plane in the first optical system between the imaging plane and the first reflection mirror 20 (imaging step). The first optical system includes the objective lens 13 and the tube lens 16. With this configuration, a clear interference image can be acquired.

Further, in the two-beam interferometer, preferably, the optical path length between the position conjugate to the imaging plane and the reflection surface of the first reflection mirror 20 in the first optical system and the optical path length between the position conjugate to the imaging plane and the reflection surface of the second reflection mirror 15 in the second optical system between the imaging plane and the second reflection mirror 15 are made equal to each other (interference step). The second optical system includes the objective lens 14 and the tube lens 16. In adjusting the optical path length between the position conjugate to the imaging plane and the reflection surface of the second reflection mirror 15 in the second optical system, it is preferable to use the focus adjustment mechanism 60. With this configuration, a further clear interference image can be acquired.

The light output from the light source 11 is split into two light beams by the beam splitter 12 to form the first light beam and the second light beam, and the first light beam and the second light beam are output from the beam splitter 12. The first light beam output from the beam splitter 12 is focused to the cell 73 in the container 70 by the objective lens 13, transmitted through the cell 73 and the bottom portion of the container 70, and reflected by the first reflection mirror 20 provided on the outer side of the bottom portion of the container 70. The first light beam reflected by the first reflection mirror 20 is input to the beam splitter 12 through the objective lens 13. The second light beam output from the beam splitter 12 is input to the reflection surface of the second reflection mirror 15 by the objective lens 14, and reflected by the reflection surface. The second light beam reflected by the reflection surface of the second reflection mirror 15 is input to the beam splitter 12 through the objective lens 14.

The first light beam input from the objective lens 13 to the beam splitter 12 and the second light beam input from the objective lens 14 to the beam splitter 12 are combined by the beam splitter 12, and interference light is output from the beam splitter 12. The interference light is passed through the tube lens 16, then split into two beams by the beam splitter 17, and received by the imager 18 and the photodetector 22. The detection signal is output from the photodetector 22 that has received the interference light, and the optical path difference between the two light beams in the two-beam interferometer is detected by the phase control unit 23 based on the detection signal. Further, by feedback control on the piezoelectric element 21 by the phase control unit 23, a state is achieved (a locked state) in which the optical path difference between the two light beams in the two-beam interferometer is stabilized at the set value. In the locked state, an interference image is acquired by the imager 18 that has received the interference light, and the interference image is output to the operation unit 30. Further, the operation unit 30 determines the phase image or the like of the object (cell 73) based on the interference image.

For example, the phase difference of the interference light is stabilized in a certain initial phase by feedback control using the piezoelectric element 21, the photodetector 22, and the phase control unit 23, and an interference image I1 is acquired by the imager 18 in the state in which the phase difference is stabilized. Subsequently, the phase difference of the interference light is stabilized in "the initial phase+π/2" using the piezoelectric element 21, the photodetector 22, and the phase control unit 23, and an interference image I2 is acquired by the imager 18 in the state in which the phase difference is stabilized. Similarly, an interference image I3 is acquired by the imager 18 in the state in which the phase difference of the interference light is stabilized in "the initial phase+π", and an interference image I4 is acquired by the imager 18 in the state in which the phase difference of the interference light is stabilized in "the initial phase+3π/2".

The operation unit 30 performs an operation of the following Formula using the four interference images I1 to I4, and determines a phase image φ (operation step). In addition, I1 to I4 and φ are the functions of the pixel position (x,y), and the operation of the following Formula is performed for each pixel. arg is an operator that acquires the argument of the complex number. i is the imaginary unit.

[Formula 2]

$$\phi = \arg\{(I1-I3)+i(I2-I4)\} \quad (2)$$

Figure 3:
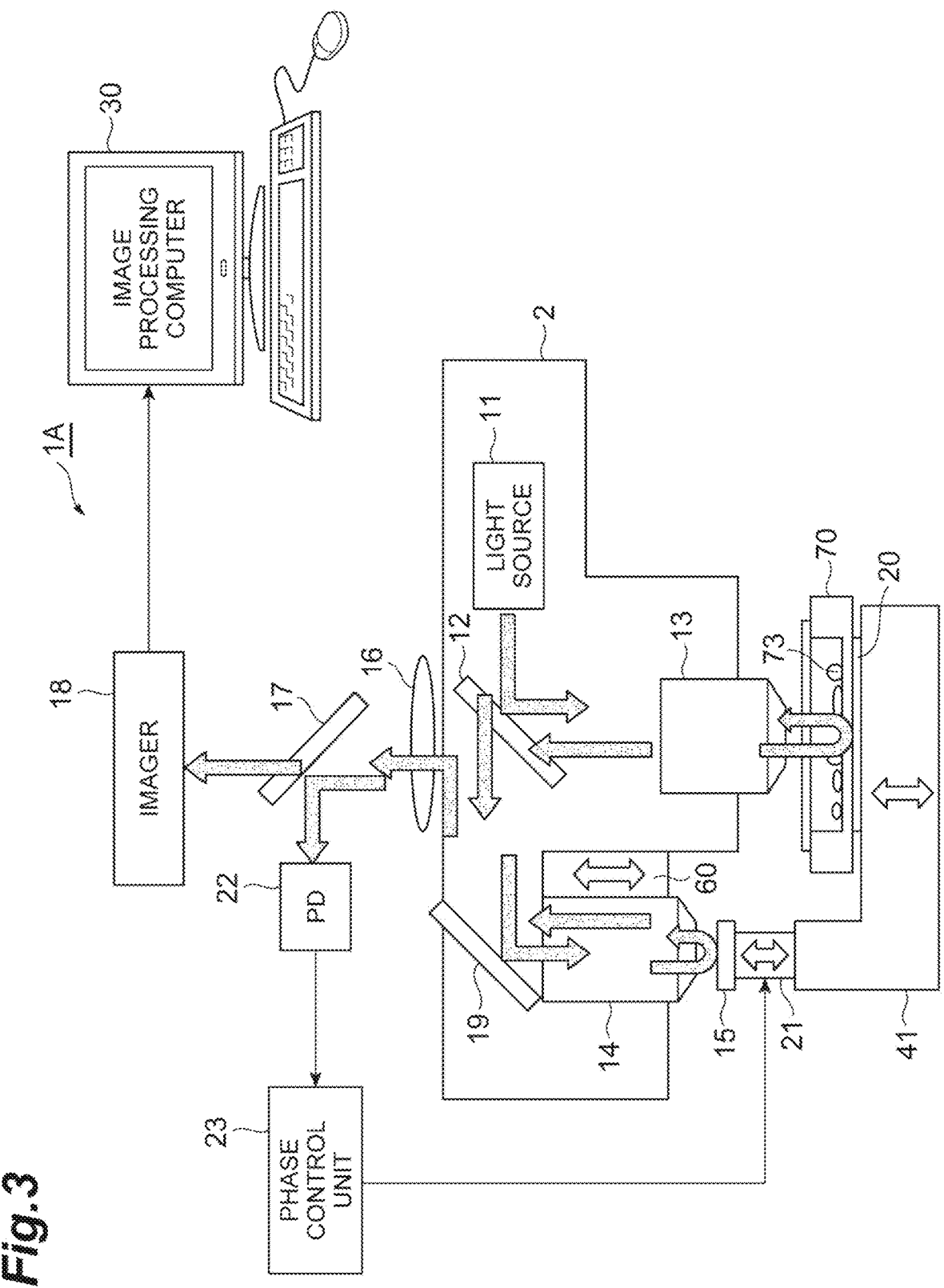
FIG. 3 is a diagram illustrating a configuration of a first modification of the interference image acquisition apparatus 1.

FIG. 3 is a diagram illustrating a configuration of a first modification of the interference image acquisition apparatus 1. In the comparison with the configuration of the interference image acquisition apparatus 1 illustrated in FIG. 1, an interference image acquisition apparatus 1A according to the first modification illustrated in FIG. 3 is different in that a reflection mirror 19 and a stage 41 are included.

The reflection mirror 19 is provided on the optical path of the second light beam between the beam splitter 12 and the objective lens 14, and reflects the second light beam. By providing the reflection mirror 19, the optical axes of the objective lens 13 and the objective lens 14 can be made in parallel with each other, and further, the reflection surfaces of the first reflection mirror 20 and the second reflection mirror 15 can be made in parallel with each other.

The stage 41 can move the container 70, the first reflection mirror 20, the piezoelectric element 21, and the second reflection mirror 15 in the direction along the optical axes of the objective lens 13 and the objective lens 14. That is, the optical path length of the first light beam and the optical path length of the second light beam can be made variable.

The stage 41 is used as an adjustment unit that adjusts the position at which the cell 73 that is an object is placed. That is, first, the stage 41 places the reflection surface of the first reflection mirror 20 at the position conjugate to the imaging plane in the first optical system, the positional relationship conjugate to each other is achieved between the reflection surface of the second reflection mirror 15 and the imaging plane using the focus adjustment mechanism 60 in the second optical system, and the optical path difference between the first optical system and the second optical system is set to the coherence length or less (interference step).

After that, the stage 41 adjusts the optical path length of the first light beam and the optical path length of the second light beam, and thus the object is placed at the position conjugate to the imaging plane in the first optical system (adjustment step). In this state, automatically, the optical path length between the position conjugate to the imaging plane and the reflection surface of the first reflection mirror 20 in the first optical system and the optical path length between the position conjugate to the imaging plane and the reflection surface of the second reflection mirror 15 in the second optical system between the imaging plane and the second reflection mirror 15 are approximately made equal to each other. With this configuration, the placement of the object can be easily adjusted, and further, the positions conjugate to the imaging plane in the first optical system and the second optical system can be easily adjusted.

In the interference step, in the placement of the reflection surface of the first reflection mirror 20 at the position conjugate to the imaging plane in the first optical system and in the placement of the reflection surface of the second reflection mirror 15 at the position conjugate to the imaging plane in the second optical system, in order to make focus adjustment easy, a mark may be provided on the reflection surface of one or both of the first reflection mirror 20 and the second reflection mirror 15 using a pigment or a micro flaw, for example. This mark is defocused when the object is imaged due to the adjustment of the optical path lengths of the first light beam and the second light beam by the stage 41, and thus, no influence is exerted on images when object images are acquired.

In addition, even when the position adjustment amounts of the first reflection mirror 20 and the second reflection mirror 15 by the stage 41 are the same, the optical conditions may be different between the first optical system and the second optical system, and this difference may vary the optical path length adjustment amounts of the first light beam and the second light beam from each other. Therefore, in adjusting the optical path length of the first light beam and the optical path length of the second light beam, preferably, the piezoelectric element 21 is driven by feedback control performed by the phase control unit 23 to maintain the phase difference constant.

Figure 14:
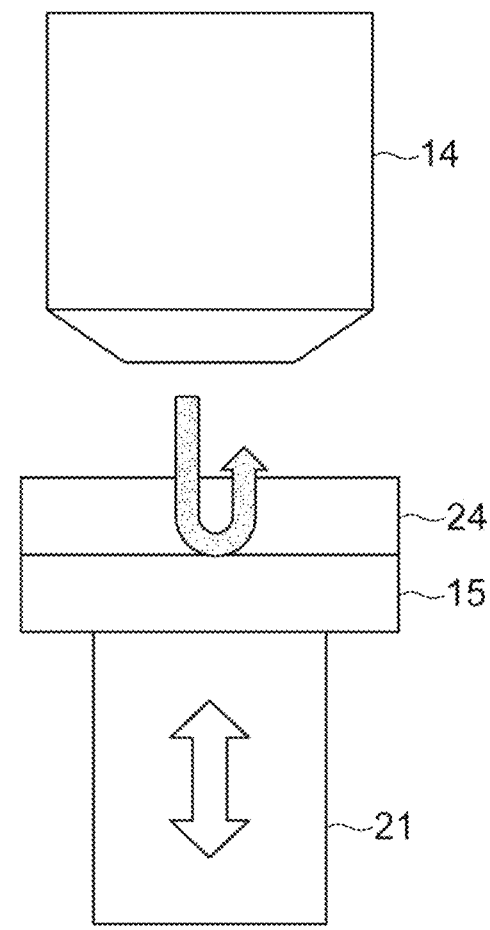
FIG. 14 is a diagram illustrating a configuration of a modification of a second optical system (reference optical system).

Further, as illustrated in FIG. 14, in order to reduce the difference in the optical conditions between the first optical system and the second optical system, a transparent layer 24 may be provided on the upper side of the reflection surface of the second reflection mirror 15. Preferably, for the material of the transparent layer 24, a material same as, or a material having the refractive index nearly equal to, the bottom portion of the container 70 present between the first reflection mirror 20 and the object in the first optical system (in FIG. 8 described later, a transparent substance 95) is used. For example, in a case where the container 70 is a bottom portion of a cell culture vessel made of polystyrene, preferably, the transparent layer 24 is also made of polystyrene. In this configuration, in the increase or decrease of the actual length of the first light beam and the actual length of the second light beam by the same distance in the adjustment step, both of the optical path length of the first light beam and the optical path length of the second light beam are increased or decreased by the same distance, which is convenient.

In addition, instead of or in addition to moving the container 70, the first reflection mirror 20, the piezoelectric element 21, and the second reflection mirror 15 by the stage 41, an optical system 2 including the light source 11, the beam splitter 12, the objective lens 13, the objective lens 14, and the reflection mirror 19 may be moved.

Figure 4:
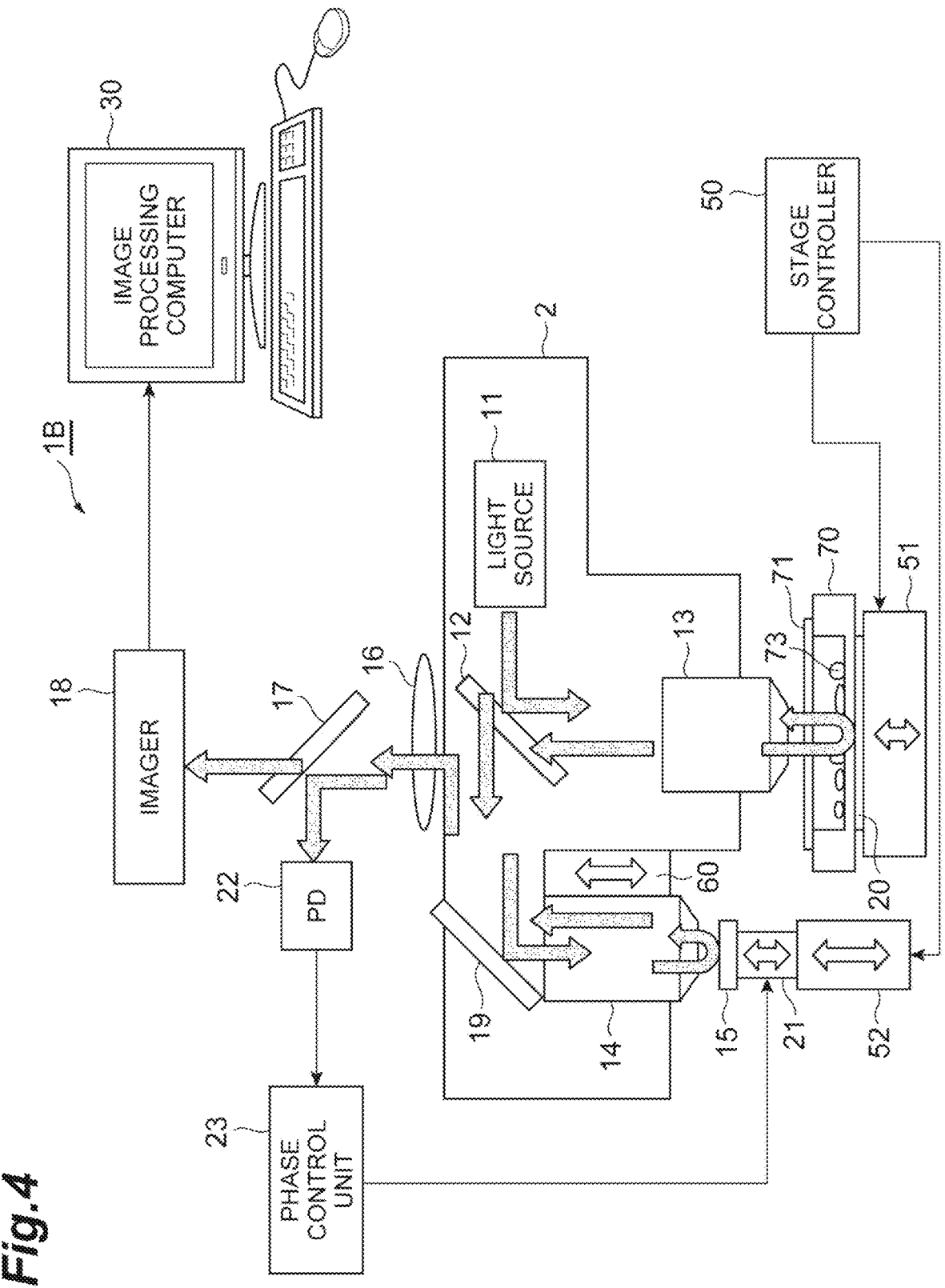
FIG. 4 is a diagram illustrating a configuration of a second modification of the interference image acquisition apparatus 1.

FIG. 4 is a diagram illustrating a configuration of a second modification of the interference image acquisition apparatus 1. In the comparison with the configuration of the interference image acquisition apparatus 1A according to the first modification illustrated in FIG. 3, an interference image acquisition apparatus 1B according to the second modification illustrated in FIG. 4 is different in that a stage controller 50, a first stage 51, and a second stage 52 are included instead of the stage 41.

The first stage 51 can move the container 70 and the first reflection mirror 20 in the direction along the optical axis of the objective lens 13. The second stage 52 can move the piezoelectric element 21 and the second reflection mirror 15 in the direction along the optical axis of the objective lens 14. That is, the optical path length of the first light beam and the optical path length of the second light beam can be made variable independently from each other. The stage controller 50 controls the operations of the first stage 51 and the second stage 52.

The stage controller 50, the first stage 51, and the second stage 52 are used as an adjustment unit that adjusts the position at which the cell 73 that is an object is placed. That is, first, the first stage 51 places the reflection surface of the first reflection mirror 20 at the position conjugate to the imaging plane in the first optical system, the optical path difference is set to the coherence length or less by the second stage 52 (and the piezoelectric element 21), and further, the positional relationship conjugate to each other is achieved between the reflection surface of the second reflection mirror 15 and the imaging plane using the focus adjustment mechanism 60 in the second optical system. After that, the first stage 51 adjusts the optical path length of the first light beam, and the second stage 52 adjusts the optical path length of the second light beam, and thus, the object is placed at the position conjugate to the imaging plane in the first optical system (adjustment step). With this configuration, the placement of the object can be easily adjusted, and further, the positions conjugate to the imaging plane in the first optical system and the second optical system can be easily adjusted.

Also in the second modification, in adjusting the optical path length of the first light beam and the optical path length of the second light beam, preferably, the piezoelectric element 21 is driven by feedback control performed by the phase control unit 23 to maintain the phase difference constant. Further, as illustrated in FIG. 14, the transparent layer 24 may be provided on the upper side of the reflection surface of the second reflection mirror 15. Further, instead of or in addition to moving the container 70 and the first reflection mirror 20 by the first stage 51 and moving the piezoelectric element 21 and the second reflection mirror 15 by the second stage 52, the optical system 2 including the light source 11, the beam splitter 12, the objective lens 13, the objective lens 14, and the reflection mirror 19 may be moved.

Figure 5:
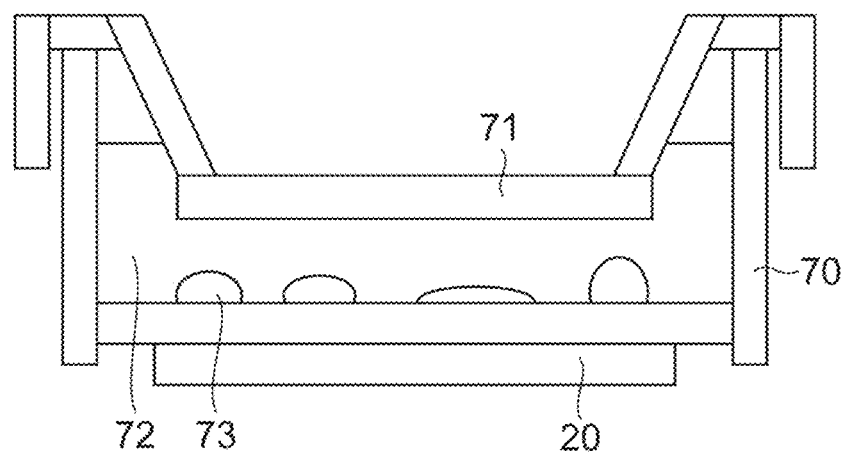
FIG. 5 is a diagram illustrating a configuration of the sample used in an example.

An example using the configuration example of the sample illustrated in FIG. 2 will be described. FIG. 5 is a diagram illustrating a configuration of the sample used in the example. As the container 70, a plastic dish of 35 mmΦ was used. The thickness of the bottom portion of the container 70 was 1 mm. The contact of the under surface of the center portion of the cover 71 with the culture solution 72 avoided the contact of the liquid surface of the culture solution 72 with the air, and this avoided the fluctuation in the liquid surface of the culture solution 72. For the cell 73 that is an object, HeLa cell was used. The magnifications of the objective lenses 13 and 14 were 10 times. The wavelength of the output light of the light source 11 was 633 nm, and the bandwidth of the output light was 3 nm. The coherence length of the light source 11 was approximately 50 µm.

Figure 6:
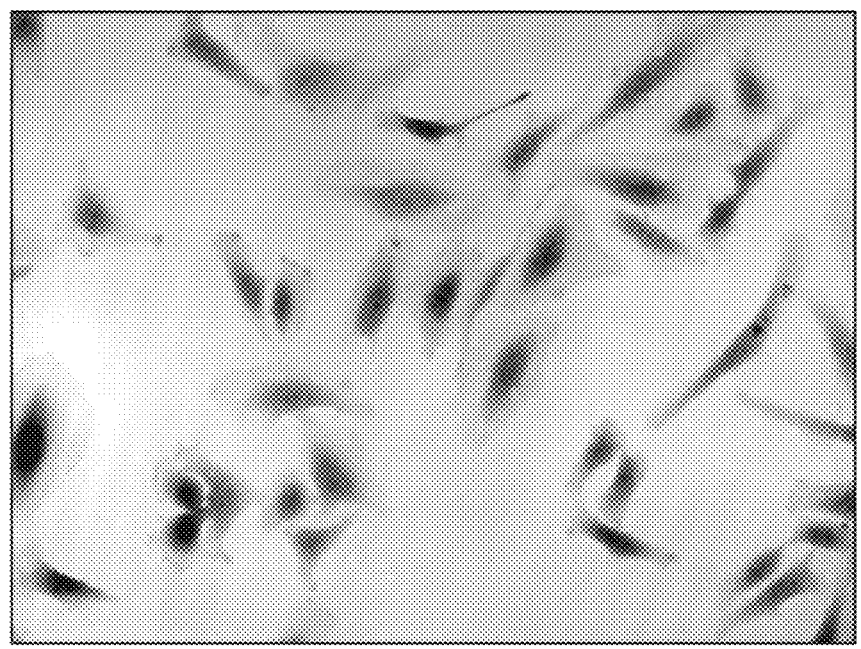
FIG. 6 is a diagram showing a phase image generated based on a plurality of interference images obtained in the example.

FIG. 6 is a diagram showing a phase image generated based on a plurality of interference images obtained in the example. In the example, clear interference images are obtained, and thus a clear phase image shown in this drawing is obtained.

Figure 7:
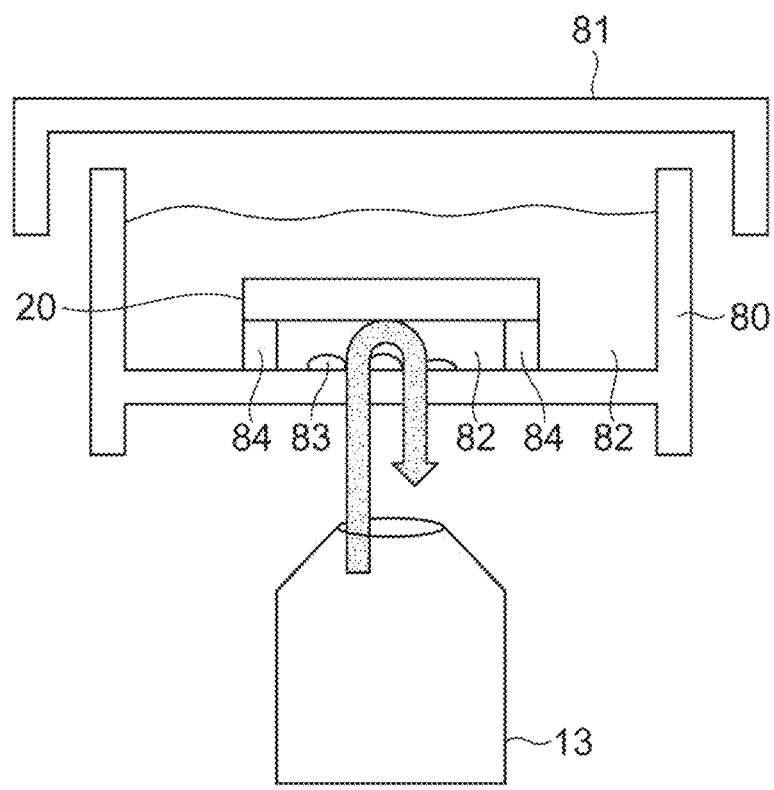
FIG. 7 is a diagram illustrating a configuration of a first modification of the sample.

FIG. 7 is a diagram illustrating a configuration of a first modification of the sample. The sample of the first modification illustrated in this drawing is preferable in a case where the objective lens 13 is a part of an inverted microscope. The object is a cell 83 in a culture solution 82 contained in a container 80. The first reflection mirror 20 is placed on the inner side of the bottom portion of the container 80 apart from the bottom portion of the container 80 with a spacer 84. At least the reflection surface of the first reflection mirror 20 is in contact with the culture solution 82. The cell 83 as the object is present in a space surrounded by the bottom portion of the container 80, the first reflection mirror 20, and the spacer 84. The upper portion of the container 80 is covered with a cover 81. That is, in this configuration example of the sample, the cell 83 is placed on one side of the bottom portion of the container 80 (transparent material), and the first reflection mirror 20 is placed on the one side of the transparent material apart from the cell 83. The first light beam output from the objective lens 13 is passed through the bottom portion of the container 80 (transparent material) and the cell 83 in sequence, and then reflected by the first reflection mirror 20.

Figure 8:
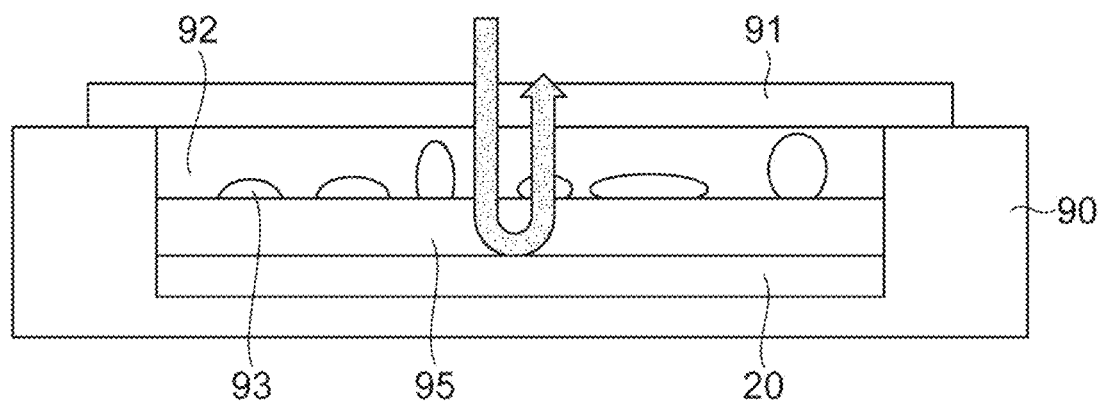
FIG. 8 is a diagram illustrating a configuration of a second modification of the sample.

FIG. 8 is a diagram illustrating a configuration of a second modification of the sample. In the sample of the second modification illustrated in this drawing, the object is a cell 93 in a culture solution 92 contained in a container 90. The first reflection mirror 20 is placed on the inner side of the bottom portion of the container 90. The first reflection mirror 20 may be a reflection enhancing coating formed on the inner side of the bottom portion of the container 90. A transparent substance 95 is placed on the reflection surface of the first reflection mirror 20, and the cell 93 as the object is placed on or in the transparent substance 95. The inside of the container 90 is sealed with a cover 91. The first light beam output from the objective lens 13 is reflected by the first reflection mirror 20 after being passed through the cell 93 and the transparent substance 95. In a case where the object is a cell, the transparent substance may be a gel substance with which the cell is cultured (for example, matrigel, collagen, gelatin, or the like).

Figure 9:
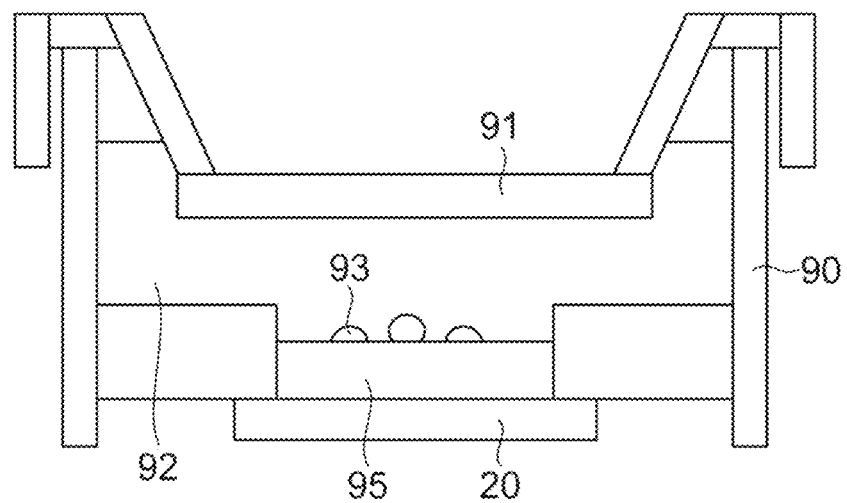
FIG. 9 is a diagram illustrating a configuration of the sample used in an example.

An example using the configuration example of the sample illustrated in FIG. 8 will be described. FIG. 9 is a diagram illustrating a configuration of the sample used in the example. As the container 90, a glass bottom dish having a reflection enhancing coating formed on the surface of the inner side of the bottom portion was used. The reflection enhancing coating was used as the first reflection mirror 20. On the first reflection mirror 20, a matrigel layer was placed as the transparent substance 95. The thickness of the matrigel layer was approximately 100 μm. The contact of the under surface of the center portion of the cover 91 with the culture solution 92 avoided the contact of the liquid surface of the culture solution 92 with the air, and this avoided the fluctuation in the liquid surface of the culture solution 92. As the cell 93 of the object, lymphatic endothelial cells of the primary culture were used. The magnifications of the objective lenses 13 and 14 were 10 times. The wavelength of the output light of the light source 11 was 633 nm.

Figure 10:
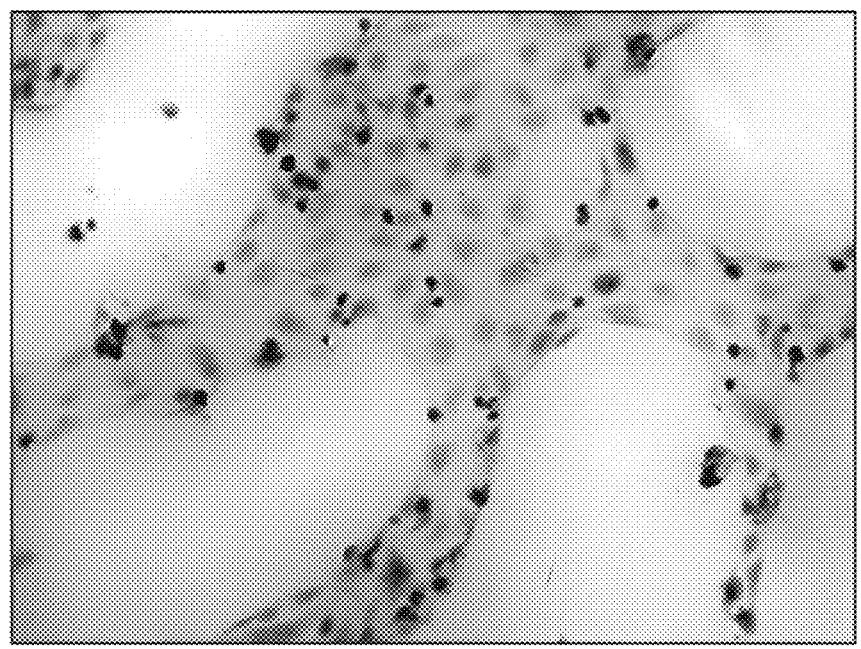
FIG. 10 is a diagram showing a phase image generated based on a plurality of interference images obtained in the example.

FIG. 10 is a diagram showing a phase image generated based on a plurality of interference images obtained in the example. Also in the example, clear interference images are obtained, and thus a clear phase image shown in this drawing is obtained.

Figure 11:
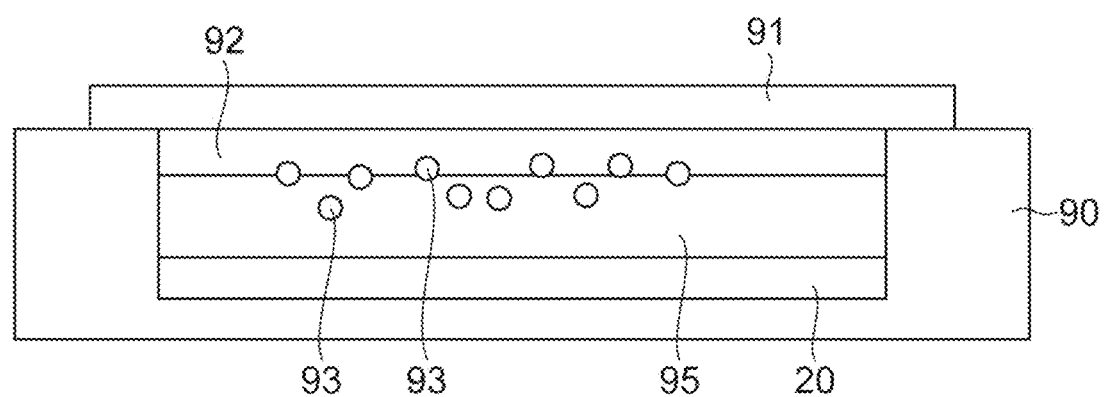
FIG. 11 is a diagram illustrating a state in which a plurality of objects are three-dimensionally distributed in the configuration example of the sample illustrated in FIG. 8.

FIG. 11 is a diagram illustrating a state in which objects are three-dimensionally distributed in the configuration example of the sample illustrated in FIG. 8. For example, it is known that using a gel substance (matrigel, collagen, gelatin, or the like) referred to as an extracellular matrix as the transparent substance 95, cells cultured on the gel substance enter the inside of the gel substance in the course of culture, three-dimensionally migrate in the inside of the gel substance, and form a tissue structure. Further, it is known that vascular endothelial cells cultured on the matrigel that is a gel substance spontaneously form a blood vessel-like or lymph vessel-like structure due to self organization in the course of culture, even in a case where the cells are dispersedly seeded. This is referred to as tube formation. Observation of occurrence of appropriate tube formation enables the determination of the property of the cell.

In the present embodiment, in a case where the objects are three-dimensionally distributed in this manner, the three-dimensional image of the object can be determined (see Non Patent Document 1). That is, in the two-beam interferometer, the position conjugate to the imaging plane in the first optical system is scanned along the optical axis of the first optical system, and the imager 18 acquires interference images at respective positions of scanning. In scanning the position conjugate to the imaging plane in the first optical system along the optical axis, preferably, the configuration of the first modification or the second modification is used. The operation unit 30 determines the phase images and the intensity images of the object for the respective positions of scanning of the conjugate position, and determines the three-dimensional image of the object based on these images.

Figure 12:
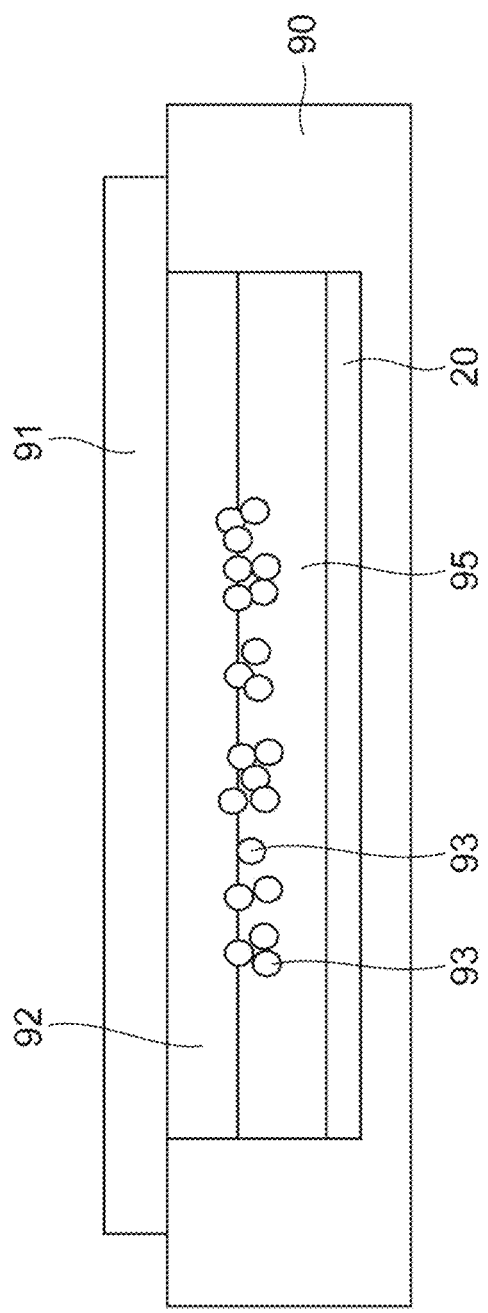
FIG. 12 is a diagram illustrating a state in which the plurality of objects are three-dimensionally distributed in the configuration example of the sample illustrated in FIG. 8, and some of the plurality of objects are three-dimensionally aggregated.

FIG. 12 is a diagram illustrating a state in which the plurality of objects are three-dimensionally distributed in the configuration example of the sample illustrated in FIG. 8 and some of the plurality of objects are three-dimensionally aggregated. In the three-dimensional distribution of the objects, the objects are in three-dimensionally close contact, and a part of the objects is placed directly above another object. For example, the cells 93 that are cultured using a gel substance (matrigel, collagen, gelatin, or the like) referred to as an extracellular matrix as the transparent substance 95 sometimes form an arrangement in which the cells are in a three-dimensionally close contact due to cell division or self organization as the culture period is prolonged. In such a three-dimensional arrangement, a part of or all the micro parts are buried in the gel substance.

Even in such a sample configuration similarly, in the two-beam interferometer, the position conjugate to the imaging plane in the first optical system is scanned along the optical axis of the first optical system, and the imager 18 acquires interference images at the respective positions of scanning, and thus, the phase images and the intensity images of the object are determined by the operation unit 30 for the respective positions of scanning of the conjugate position, and the three-dimensional image of the object can be determined based on these images.

Figure 13:
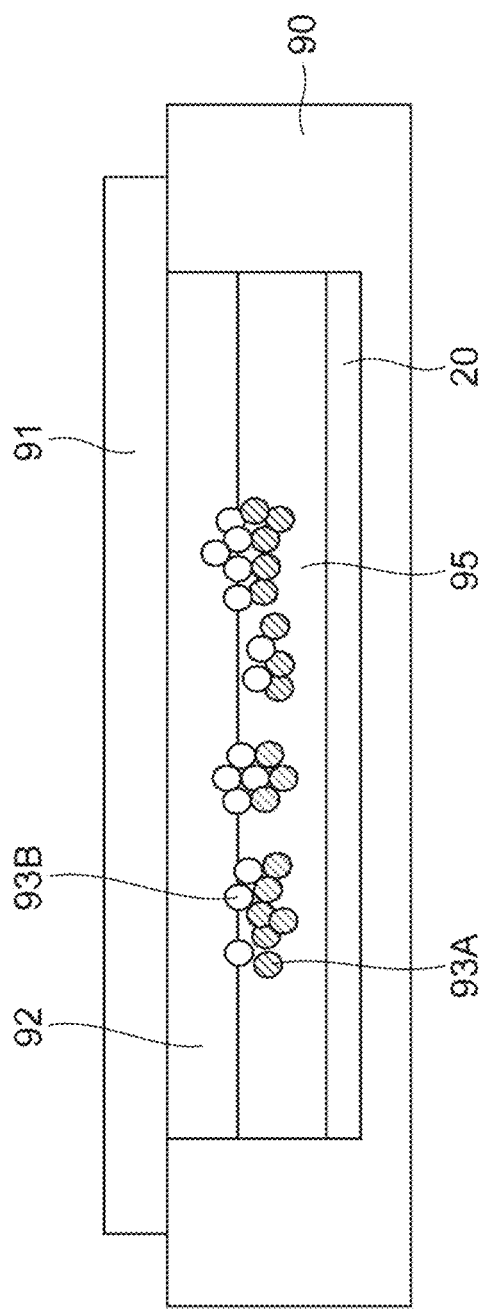
FIG. 13 is a diagram illustrating a state in which the plurality of objects are three-dimensionally distributed in the configuration example of the sample illustrated in FIG. 8, some of the plurality of objects are three-dimensionally aggregated, and the aggregate includes a plurality of types of objects.

FIG. 13 is a diagram illustrating a state in which the plurality of objects are three-dimensionally distributed in the configuration example of the sample illustrated in FIG. 8, some of the plurality of objects are three-dimensionally aggregated, and the aggregate includes a plurality of types of objects. For example, a configuration may be provided in which a gel substance (matrigel, collagen, gelatin, or the like) referred to as an extracellular matrix is used as the transparent substance 95, first type cells 93A are first cultured and buried in the inside of the transparent substance 95, and subsequently, second type cells 93B are cultured on the surface of the transparent substance 95.

Under such culture conditions, the second type cell 93B migrates the position at which the cell is in three-dimensionally close contact with the first type cell 93A due to the influence of chemical substances, for example, output from the first type cell 93A previously cultured, and forms a three-dimensional structure. For example, fibroblasts are used as the first type cells, and vascular endothelial cells of the blood vessel or the lymph vessel are used as the second type cells, and a sample that imitates the structure of the lymph vessel or the blood vessel in the living body can be formed.

Also in such a sample configuration similarly, in the two-beam interferometer, the position conjugate to the imaging plane in the first optical system is scanned along the optical axis of the first optical system, the imager 18 acquires interference images at the respective positions of scanning, and thus, the phase images and the intensity images of the object are determined by the operation unit 30 for the respective positions of scanning of the conjugate position, and the three-dimensional image of the object can be determined based on these images. In the scanning of the conjugate position, the conditions may be set such that the first type cell 93A buried in the inside of the transparent substance 95 is observed, or the conditions may be set such that the second type cell 93B placed on the first type cell is observed.

As described above, in the present embodiment, in a case where the reflection mirror and the object are apart from each other, a clear interference image can be acquired, and further, a clear phase image can be acquired. In the configuration example of the sample illustrated in FIG. 2, the reflection enhancing coating is not necessarily applied to the inner side of the bottom portion of the container, and thus a dish that is inexpensively commercially available can be used as a container. Further, in the configuration example of the sample illustrated in FIG. 2, in a case where the container is expendable because the objects are infectious cells, for example, the container only has to be discarded after measurement, and thus running costs are low, and waste amounts are also suppressed.

Also in the configuration example of the sample illustrated in FIG. 7, the reflection enhancing coating is not necessarily applied to the inner side of the bottom portion of the container, and thus a dish that is inexpensively commercially available can be used as a container. In the configuration example of the sample illustrated in FIG. 8, three-dimensional observation can be performed on the object.

The interference image acquisition apparatus and the interference image acquisition method are not limited to the embodiments and the configuration examples described above, and can be variously modified.

The interference image acquisition apparatus of the above embodiment is configured to include (1) a light source for outputting incoherent light, (2) a two-beam interferometer for splitting the light output from the light source into a first light beam and a second light beam, combining the first light beam transmitted through an object placed on an optical path of the first light beam and reflected by a first reflection mirror and the second light beam reflected by a second reflection mirror, and outputting interference light, and (3) an imager having an imaging plane for receiving the interference light output from the two-beam interferometer, and for acquiring an interference image of the object, and (4) in the two-beam interferometer, the first reflection mirror is placed apart from the object, and an optical path difference between an optical path length of the first light beam reflected by the first reflection mirror and an optical path length of the second light beam reflected by the second reflection mirror is set to a coherence length of the light output from the light source or less, and the imager acquires the interference image in a state in which the object is placed at a position conjugate to the imaging plane in a first optical system between the imaging plane and the first reflection mirror.

In the above interference image acquisition apparatus, in the two-beam interferometer, an optical path length between the position conjugate to the imaging plane in the first optical system and a reflection surface of the first reflection mirror and an optical path length between a position conjugate to the imaging plane in a second optical system between the imaging plane and the second reflection mirror and a reflection surface of the second reflection mirror may be equal to each other.

In the above interference image acquisition apparatus, the two-beam interferometer may have a transparent layer provided on the reflection surface of the second reflection mirror.

In the above interference image acquisition apparatus, in the two-beam interferometer, the optical path length of the first light beam and the optical path length of the second light beam may be variable, and the apparatus may further include an adjustment unit for placing the reflection surface of the first reflection mirror at the position conjugate to the imaging plane in the first optical system, setting the optical path difference to the coherence length or less, then adjusting the optical path length of the first light beam and the optical path length of the second light beam, and placing the object at the position conjugate to the imaging plane in the first optical system.

In the above interference image acquisition apparatus, the apparatus may further include a phase control unit for feedback-controlling a phase difference based on a detection result of the phase difference between the first light beam and the second light beam in combining in the two-beam interferometer, and the adjustment unit may maintain the phase difference constant by the phase control unit in adjusting the optical path length of the first light beam and the optical path length of the second light beam.

In the above interference image acquisition apparatus, the apparatus may further include an operation unit for determining a phase image of the object based on a plurality of interference images acquired by the imager.

In the above interference image acquisition apparatus, the operation unit may determine the phase image and an intensity image of the object based on the plurality of interference images acquired by the imager.

In the above interference image acquisition apparatus, in the two-beam interferometer, the position conjugate to the imaging plane in the first optical system may be scanned along an optical axis of the first optical system, the imager may acquire the interference images at respective positions of scanning, and the operation unit may determine the phase images and the intensity images for the respective positions of scanning, and may determine a three-dimensional image of the object based on the phase images and the intensity images.

The interference image acquisition method of the above embodiment is configured to include (1) an interference step of, in a two-beam interferometer, splitting incoherent light output from a light source into a first light beam and a second light beam, combining the first light beam transmitted through an object placed on an optical path of the first light beam and reflected by a first reflection mirror and the second light beam reflected by a second reflection mirror, and outputting interference light, and (2) an imaging step of acquiring an interference image of the object by an imager having an imaging plane for receiving the interference light output from the two-beam interferometer, and (3) in the interference step, in the two-beam interferometer, the first reflection mirror is placed apart from the object, and an optical path difference between an optical path length of the first light beam reflected by the first reflection mirror and an optical path length of the second light beam reflected by the second reflection mirror is set to a coherence length of the light output from the light source or less, and in the imaging step, the interference image is acquired by the imager in a state in which the object is placed at a position conjugate to the imaging plane in a first optical system between the imaging plane and the first reflection mirror.

In the above interference image acquisition method, in the interference step, in the two-beam interferometer, an optical path length between the position conjugate to the imaging plane in the first optical system and a reflection surface of the first reflection mirror and an optical path length between a position conjugate to the imaging plane in a second optical system between the imaging plane and the second reflection mirror and a reflection surface of the second reflection mirror may be equal to each other.

In the above interference image acquisition method, in the two-beam interferometer, a transparent layer may be provided on the reflection surface of the second reflection mirror.

In the above interference image acquisition method, in the two-beam interferometer, the optical path length of the first light beam and the optical path length of the second light beam may be variable, and the method may further include an adjustment step of placing the reflection surface of the first reflection mirror at the position conjugate to the imaging plane in the first optical system, setting the optical path difference to the coherence length or less, then adjusting the optical path length of the first light beam and the optical path length of the second light beam, and placing the object at the position conjugate to the imaging plane in the first optical system.

In the above interference image acquisition method, in the adjustment step, by a phase control unit for feedback-controlling a phase difference based on a detection result of the phase difference between the first light beam and the second light beam in combining in the two-beam interferometer, the phase difference may be maintained constant in adjusting the optical path length of the first light beam and the optical path length of the second light beam.

In the above interference image acquisition method, the method may further include an operation step of determining a phase image of the object based on a plurality of interference images acquired by the imager.

In the above interference image acquisition method, in the operation step, the phase image and an intensity image of the object may be determined based on the plurality of interference images acquired by the imager.

In the above interference image acquisition method, in the interference step, in the two-beam interferometer, the position conjugate to the imaging plane in the first optical system may be scanned along an optical axis of the first optical system, in the imaging step, the interference images may be acquired by the imager at respective positions of scanning, and in the operation step, the phase images and the intensity images may be determined for the respective positions of scanning, and a three-dimensional image of the object may be determined based on the phase images and the intensity images.

In the above interference image acquisition method, the object may be placed on one side of a transparent material, and the first reflection mirror may be placed on the other side of the transparent material, and in the interference step, the first light beam being passed through the object and the transparent material in sequence may be reflected by the first reflection mirror.

In the above interference image acquisition method, the object may be placed on one side of a transparent material, and the first reflection mirror may be placed apart from the object on the one side of the transparent material, and in the interference step, the first light beam being passed through the transparent material and the object in sequence may be reflected by the first reflection mirror.

In the above interference image acquisition method, a transparent substance may be placed on the reflection surface of the first reflection mirror, and the object may be placed on or in the transparent substance, and in the interference step, the first light beam being passed through the object and the transparent substance may be reflected by the first reflection mirror.

In the above interference image acquisition method, the object may be a cell, and the transparent substance may be a gel substance.

In the above interference image acquisition method, the object may be a plurality of cells, and at least one cell in the plurality of cells may be placed in the transparent substance, and the plurality of cells may be in three-dimensionally close contact.

In the above interference image acquisition method, the object may be a plurality of cells of different types, and the plurality of cells of different types may form a layer in an inside or on a surface of the transparent substance.

INDUSTRIAL APPLICABILITY

The embodiments may be used as an apparatus and a method that can acquire a clear interference image in a case where a reflection mirror and an object are apart from each other.

REFERENCE SIGNS LIST 1, 1A, 1B—interference image acquisition apparatus, 11—light source, 12—beam splitter, 13, 14—objective lens, 15—second reflection mirror, 16—tube lens, 17—beam splitter, 18—imager, 19—reflection mirror, 20—first reflection mirror, 21—piezoelectric element, 22—photodetector, 23—phase control unit, 24—transparent layer, 30—operation unit, 41—stage, 50—stage controller, 51—first stage, 52—second stage, 60—focus adjustment mechanism, 61—optical path difference adjustment mechanism, 70—container, 71—cover, 72—culture solution, 73—cell, 80—container, 81—cover, 82—culture solution, 83—cell, 84—spacer, 90—container, 91—cover, 92—culture solution, 93—cell, 93A—first type cell, 93B—second type cell, 95—transparent substance.

The invention claimed is:

1. An interference image acquisition apparatus comprising:
a light source configured to output incoherent light;
a two-beam interferometer configured to split the light output from the light source into a first light beam and a second light beam, combine the first light beam transmitted through an object placed on an optical path of the first light beam and reflected by a first reflection mirror and the second light beam reflected by a second reflection mirror, and output interference light; and
an imager having an imaging plane configured to receive the interference light output from the two-beam interferometer, the imager configured to acquire an interference image of the object, wherein
in the two-beam interferometer, the first reflection mirror is placed apart from the object, and an optical path difference between an optical path length of the first light beam reflected by the first reflection mirror and an optical path length of the second light beam reflected by the second reflection mirror is set to a coherence length of the light output from the light source or less, and
the imager is configured to acquire the interference image in a state in which the object is placed at a position conjugate to the imaging plane in a first optical system between the imaging plane and the first reflection mirror.

2. The interference image acquisition apparatus according to claim 1, wherein in the two-beam interferometer, an optical path length between the position conjugate to the imaging plane in the first optical system and a reflection surface of the first reflection mirror and an optical path length between a position conjugate to the imaging plane in a second optical system between the imaging plane and the second reflection mirror and a reflection surface of the second reflection mirror are equal to each other.

3. The interference image acquisition apparatus according to claim 1, wherein the two-beam interferometer has a transparent layer provided on the reflection surface of the second reflection mirror.

4. The interference image acquisition apparatus according to claim 1, wherein in the two-beam interferometer, the optical path length of the first light beam and the optical path length of the second light beam are variable, and the apparatus further comprises an adjustment unit configured to place the reflection surface of the first reflection mirror at the position conjugate to the imaging plane in the first optical system, set the optical path difference to the coherence length or less, then adjust the optical path length of the first light beam and the optical path length of the second light beam, and place the object at the position conjugate to the imaging plane in the first optical system.

5. The interference image acquisition apparatus according to claim 4, further comprising a phase control unit configured to feedback-control a phase difference based on a detection result of the phase difference between the first light beam and the second light beam in combining in the two-beam interferometer, wherein the adjustment unit is configured to maintain the phase difference constant by the phase control unit in adjusting the optical path length of the first light beam and the optical path length of the second light beam.

6. The interference image acquisition apparatus according to claim 1, further comprising an operation unit configured to determine a phase image of the object based on a plurality of interference images acquired by the imager.

7. The interference image acquisition apparatus according to claim 6, wherein the operation unit is configured to determine the phase image and an intensity image of the object based on the plurality of interference images acquired by the imager.

8. The interference image acquisition apparatus according to claim 7, wherein in the two-beam interferometer, the position conjugate to the imaging plane in the first optical system is scanned along an optical axis of the first optical system, the imager is configured to acquire the interference images at respective positions of scanning, and the operation unit is configured to determine the phase images and the intensity images for the respective positions of scanning, and determine a three-dimensional image of the object based on the phase images and the intensity images.

9. An interference image acquisition method comprising:

an interference step of, in a two-beam interferometer, splitting incoherent light output from a light source into a first light beam and a second light beam, combining the first light beam transmitted through an object placed on an optical path of the first light beam and reflected by a first reflection mirror and the second light beam reflected by a second reflection mirror, and outputting interference light; and an imaging step of acquiring an interference image of the object by an imager having an imaging plane configured to receive the interference light output from the two-beam interferometer, wherein in the interference step, in the two-beam interferometer, the first reflection mirror is placed apart from the object, and an optical path difference between an optical path length of the first light beam reflected by the first reflection mirror and an optical path length of the second light beam reflected by the second reflection mirror is set to a coherence length of the light output from the light source or less, and in the imaging step, the interference image is acquired by the imager in a state in which the object is placed at a position conjugate to the imaging plane in a first optical system between the imaging plane and the first reflection mirror.

10. The interference image acquisition method according to claim 9, wherein in the interference step, in the two-beam interferometer, an optical path length between the position conjugate to the imaging plane in the first optical system and a reflection surface of the first reflection mirror and an optical path length between a position conjugate to the imaging plane in a second optical system between the imaging plane and the second reflection mirror and a reflection surface of the second reflection mirror are equal to each other.

11. The interference image acquisition method according to claim 9, wherein in the two-beam interferometer, a transparent layer is provided on the reflection surface of the second reflection mirror.

12. The interference image acquisition method according to claim 9, wherein in the two-beam interferometer, the optical path length of the first light beam and the optical path length of the second light beam are variable, and the method further comprises an adjustment step of placing the reflection surface of the first reflection mirror at the position conjugate to the imaging plane in the first optical system, setting the optical path difference to the coherence length or less, then adjusting the optical path length of the first light beam and the optical path length of the second light beam, and placing the object at the position conjugate to the imaging plane in the first optical system.

13. The interference image acquisition method according to claim 12, wherein in the adjustment step, by a phase control unit configured to feedback-control a phase difference based on a detection result of the phase difference between the first light beam and the second light beam in combining in the two-beam interferometer, the phase difference is maintained constant in adjusting the optical path length of the first light beam and the optical path length of the second light beam.

14. The interference image acquisition method according to claim 9, further comprising an operation step of determining a phase image of the object based on a plurality of interference images acquired by the imager.

15. The interference image acquisition method according to claim 14, wherein in the operation step, the phase image and an intensity image of the object are determined based on the plurality of interference images acquired by the imager.

16. The interference image acquisition method according to claim 15, wherein in the interference step, in the two-beam interferometer, the position conjugate to the imaging plane in the first optical system is scanned along an optical axis of the first optical system, in the imaging step, the interference images are acquired by the imager at respective positions of scanning, and in the operation step, the phase images and the intensity images are determined for the respective positions of scanning, and a three-dimensional image of the object is determined based on the phase images and the intensity images.

17. The interference image acquisition method according to claim 9, wherein the object is placed on one side of a transparent material, and the first reflection mirror is placed on the other side of the transparent material, and in the interference step, the first light beam being passed through the object and the transparent material in sequence is reflected by the first reflection mirror.

18. The interference image acquisition method according to claim 9, wherein
the object is placed on one side of a transparent material, and the first reflection mirror is placed apart from the object on the one side of the transparent material, and
in the interference step, the first light beam being passed through the transparent material and the object in sequence is reflected by the first reflection mirror.

19. The interference image acquisition method according to claim 9, wherein
a transparent substance is placed on the reflection surface of the first reflection mirror, and the object is placed on or in the transparent substance, and
in the interference step, the first light beam being passed through the object and the transparent substance is reflected by the first reflection mirror.

20. The interference image acquisition method according to claim 19, wherein the object is a cell, and the transparent substance is a gel substance.

21. The interference image acquisition method according to claim 19, wherein the object is a plurality of cells, and at least one cell in the plurality of cells is placed in the transparent substance, and the plurality of cells are in three-dimensionally close contact.

22. The interference image acquisition method according to claim 19, wherein the object is a plurality of cells of different types, and the plurality of cells of different types forms a layer in an inside or on a surface of the transparent substance.

* * * * *